United States Patent [19]

Saragossi

[11] 4,114,272

[45] Sep. 19, 1978

[54] PROCESS FOR THE MANUFACTURE OF DENTAL PROSTHESES

[76] Inventor: Albert Saragossi, 10, rue du Four, Paris, France, 75006

[21] Appl. No.: 683,573

[22] Filed: May 5, 1976

[51] Int. Cl.$^2$ .......................... A61C 5/08; B05D 1/08
[52] U.S. Cl. ............................................. 32/8; 427/2; 427/423; 428/680
[58] Field of Search ....................... 427/2, 423, 376 C; 32/8; 264/17; 428/680

[56] References Cited

U.S. PATENT DOCUMENTS

| 2,463,551 | 3/1949 | Myerson et al. | 427/2 |
|---|---|---|---|
| 3,716,418 | 2/1973 | Kochaui | 32/8 X |
| 3,786,565 | 1/1974 | Jarrault | 32/8 |
| 3,928,913 | 12/1975 | Schaffer | 32/8 |
| 3,942,230 | 3/1976 | Nalband | 427/423 X |
| 3,996,398 | 12/1976 | Manfredi | 427/423 X |
| 4,038,752 | 8/1977 | Phelps et al. | 32/8 X |

FOREIGN PATENT DOCUMENTS 2,106,013  9/1971  Fed. Rep. of Germany ................ 32/8

*Primary Examiner*—Shrive P. Beck
*Attorney, Agent, or Firm*—William Anthony Drucker

[57] ABSTRACT

Process for the manufacture of dental prostheses comprising a metallic substructure made from a nickel based alloy and coating portions made from ceramic or plastic material, wherein the substructure surfaces to receive the coating portions are metallized.

2 Claims, No Drawings

PROCESS FOR THE MANUFACTURE OF DENTAL PROSTHESES

BACKGROUND OF THE INVENTION

The present invention relates to the manufacture of dental prostheses and more particularly to joined prostheses.

It is known that that prostheses have a metallic substructure which is fixed to the maxillary arch and ceramic crowns covered with a cermaic material or synthetic resins made by casting in a mould, followed by, if applicable, an appropriate heat treatment. The conventional procedure consisting of using a substructure made from precious alloys ensures an adequate connection between the coating and the substructure, the molten coating diffusing into the crystalline structure of the precious metal.

However, for several years now nickel-based alloys containing, for example, chromium, molybdenum or cobalt have been used for making a less complicated substructure. Prostheses made in this way have interesting qualities and a high corrosion resistance. However, the connection between the coating and the substructure is very inadequate and unreliable, the coating only adhering as a result of fritting. The coating material sometimes has a tendency to crack, break or separate from its support, despite the palliatives used (creation of a mechanical retention effect for example by hollowing out).

BRIEF SUMMARY OF THE INVENTION

The invention aims at obviating this disadvantage and has for its object a process for the manufacture of dental prostheses of the type comprising a metallic substructure made from a nickel-based alloy and coating portions, wherein the substructure surfaces which are to receive the coating portions are metallised.

The deposition of of an appropriate alloy on the substructure alloy makes it possible to obtain a perfect mechanical retention, whereby the coefficient of expansion and the surface state of the receiving shell or shield deposited, can be controlled.

DETAILED DESCRIPTION OF THE PREFERRED EMBODIMENTS

The invention will be better understood from the following description, in non-limitative example of performance thereof.

The prostheses substructure is produced in per se known manner from an alloy with the following weight composition:
C: 0.25%
Cr: 5.00%
B: 1.25%
Si: 4.00%
Fe: 2.00%
Ni: the remainder.

Once the conventional operations of roughing down, adjustment and assembly of the substructure elements have been performed, the surfaces which are to receive the coating undergo coarse grained sand blasting, for example, by means of Fontainebleau, sand or corundum and the dust is then removed by means of compessed air.

The portions to be metallised are then placed on a refractory block, whilst preventing any pollution, particularly with the hands of the operator.

Metallisation is performed with a fine powder alloy (50 microns for example) with the following weight composition:
Cr 19.0%
B 0.8%
Ni 17.0%
Si 8.0%
W 4.0%
C 0.4%
Co the remainder.

The alloy powder is sprayed on to the refractory block by means of a commercially available blowpipe gun e.g. Fusewelder Colmonoy type X6 with nozzle No. 24, Entalloy model A with nozzle No. 1, or Chpolansky No. 13005, with nozzle No. 1.

The gun is supplied with a mixture of oxygen and acetylene and a neutral flame setting is used. When the flame has heated the member to 900° C. the lever controlling the funnel containing the metallic powder to be sprayed, is pressed. During the spraying time of about 20 seconds, the temperature is held at 900° C.

The operator keeps the member under constant observation to ensure that spraying takes place perpendicularly to the different surfaces to be metallised and so that the gun can be removed by lateral displacement when the deposit thickness is considered adequate (less than 1/10 mm). The metallised member will have assumed a bright red colour.

The member is left to cool on the refractory block, after which it is ready to receive its coating. The coating operation is performed in the conventional manner, for example, using a Ceramco type ceramic or an acrylic resin which can be used hot or cold.

Obviously the composition of the metallisation alloy must be adapted to that of the base alloy and the spraying temperature can also vary. The above example correponds to a base alloy with a melting temperature of 1220° C. and a metallisation alloy with a melting range of 1105° to 1150° C. However, in order to obtain a suitable adhesion of the deposit to the substrate, the spraying temperature must be well above that used in conventional industrial metallisation operations. This temperature can vary between 900° and 1200° C. depending on the nature of the base alloy.

The procedure used is adapted to the requirements of dental prostheses. In particular, the substructure surfaces which do not receive a coating must be protected (to this end the surfaces to be protected are, for example, covered with a preparation based on whiting). The composition of the metallic deposit must be selected both to bring about a coefficient of expansion which is compatible with that of the coating and to permit an adequate penetration of the deposit particles into the substrate metal with a view to obtaining a satisfactoy mechanical adhesion. It is fundamentally a question of obtaining an adequate bond between the metallised substructure and the ceramic or plastic coating. Experience has shown that this bond is better than that obtained with the conventional procedure using gold alloys.

The invention is not limited to the embodiments described hereinbefore and various modifications can be made thereto without passing beyond the scope of the invention.

What is claimed is:

1. A process for the manufacture of dental prosthesis comprising a metallic alloy substructure consisting of by weight 87.5% nickel, 5% chromium, 1.25% boron, 4% silicon, 2% iron and 0.25% carabon and various layers of dental ceramic, said process comprising (a) preheating said metallic alloy substructure with a flame to a temperature of 900° C.-1200° C., (b) projecting a metal alloy powder having a particle size of 50 microns and consisting of 50.8% cobalt, 17.0% nickel, 19% chromium, 0.8% boron, 8.0% silicon, 4.0% tungsten and 0.4% carbon by weight through said flame and onto said preheated metallic alloy substructure, (c) terminating the projecting step when a coating having a maximum thickness of about 1/10th of a millimeter has been deposited on said substrate, and then applying to said coating various layers of dental ceramic.

2. A dental prosthesis obtained by the process according to claim 1.

* * * * *